(12) United States Patent
Schmidt

(10) Patent No.: US 6,656,106 B2
(45) Date of Patent: Dec. 2, 2003

(54) DEVICE FOR CHECKING SEEDS IN BRACHYTHERAPY NEEDLE

(76) Inventor: Bruno Schmidt, 100 Cunningham Dr., New Smyrna Beach, FL (US) 32168

( * ) Notice: Subject to any disclaimer, the term of this patent is extended or adjusted under 35 U.S.C. 154(b) by 265 days.

(21) Appl. No.: 09/930,904

(22) Filed: Aug. 17, 2001

(65) Prior Publication Data

US 2003/0036673 A1 Feb. 20, 2003

(51) Int. Cl.[7] .............. A61M 3/00; A61N 5/00
(52) U.S. Cl. ............................................... 600/7
(58) Field of Search .................... 600/1–8; 604/16, 604/83, 60–64, 51, 59, 164

(56) References Cited

U.S. PATENT DOCUMENTS

| | | | |
|---|---|---|---|
| 5,242,373 A | * | 9/1993 | Scott et al. ............... 600/7 |
| 5,906,574 A | * | 5/1999 | Kan ........................... 600/7 |
| 5,928,130 A | * | 7/1999 | Schmidt .................... 600/7 |
| 5,938,583 A | * | 8/1999 | Grimm ...................... 600/7 |
| 6,530,875 B1 | * | 3/2003 | Taylor et al. ............. 600/7 |

* cited by examiner

Primary Examiner—Samuel G. Gilbert
(74) Attorney, Agent, or Firm—Stanley M. Miller

(57) ABSTRACT

An apparatus and method for visually verifying the quantity of seeds and spacers in a brachytherapy needle. In a first embodiment, the needle is pointed upwardly and seeds and spacers slide from a lumen of the needle, under the influence of gravity, into the lumen of a clear tube that is positioned in axial alignment with the lumen of the needle by a hub. In a second embodiment, the needle is received within the lumen of the clear tube and a stylet is used to push a string of bone wax, seeds, and spacers from the lumen of the needle into the lumen of the clear tube for visual verification. A plunger rod is introduced into the proximal end of the clear tube to push the string back into the needle and the clear tube and plunger are removed to enable use of the needle. In both embodiments, the plunger rod is fully inserted into the clear tube during shipment to prevent unwanted displacement of the seeds and spacers from the needle.

16 Claims, 2 Drawing Sheets

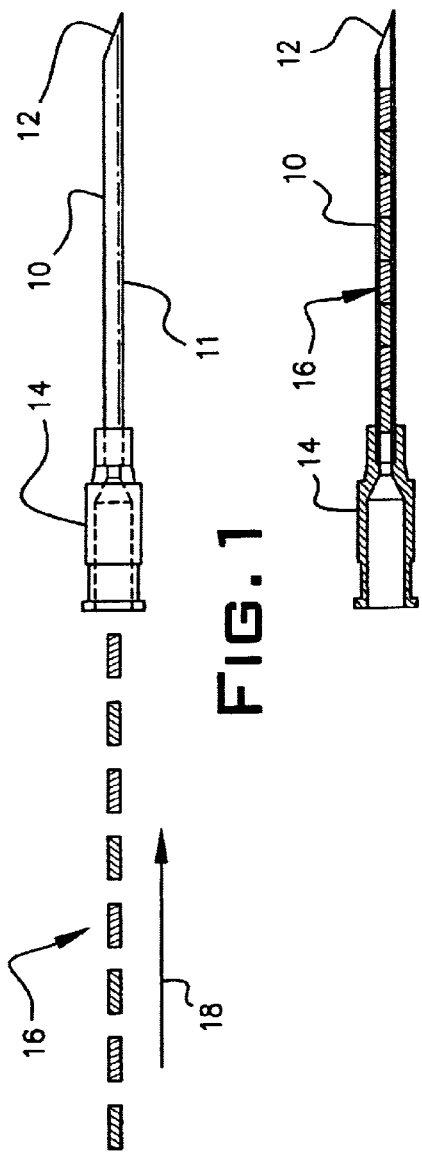
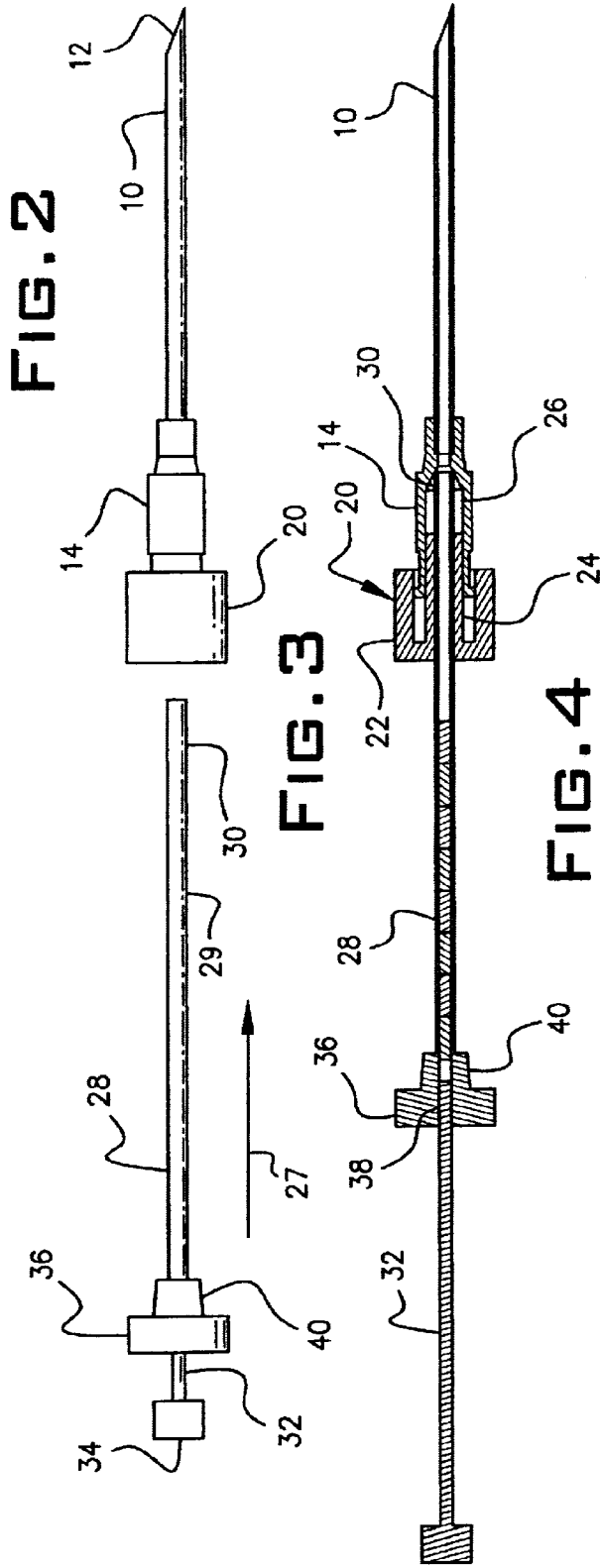

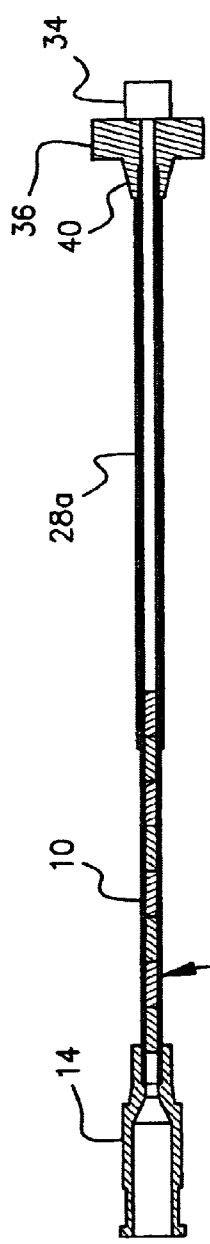
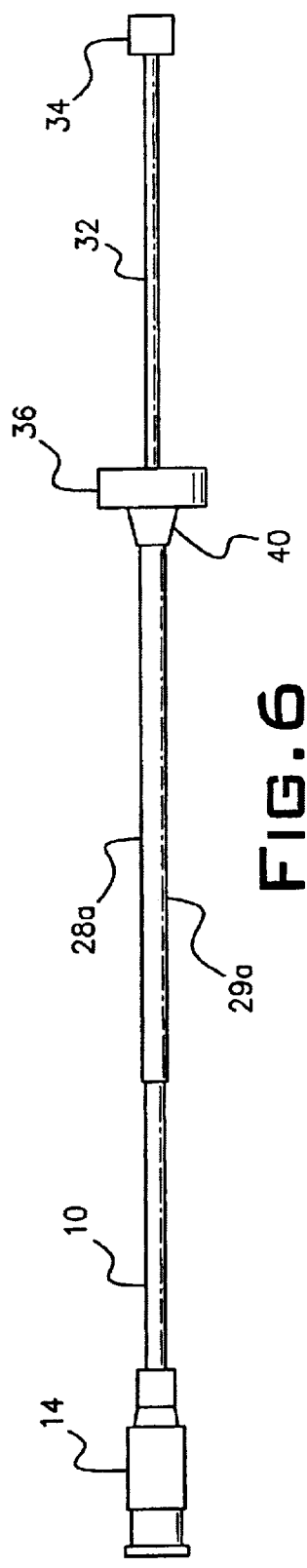
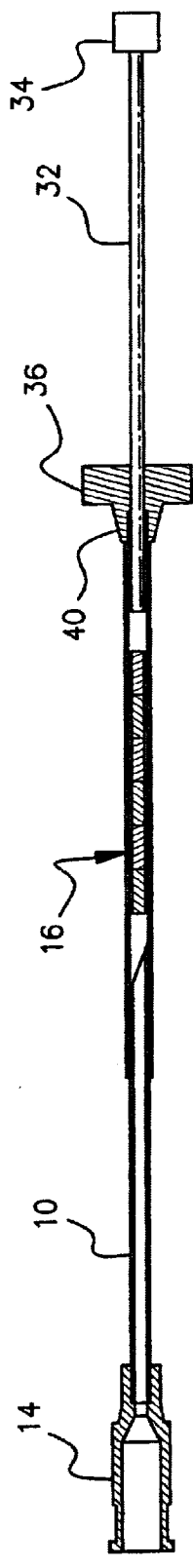

DEVICE FOR CHECKING SEEDS IN BRACHYTHERAPY NEEDLE

BACKGROUND OF THE INVENTION

1. Field of the Invention

This invention relates, generally, to medical devices. More specifically, it relates to a device for checking and verifying the number of seeds and spacers loaded inside a brachytherapy seed implantation needle.

2. Description of the Prior Art

It is easy for a physician implanting radioactive seeds in a prostate gland or other tissue to lose count of the number of seeds that have been implanted in a procedure. The number of seeds to be planted is usually a large number, and the difficulty of maintaining an accurate count of the seeds while performing the procedure is obvious.

If the physician receives a pre-loaded needle from a physicist or nuclear pharmacy, he may want to verify the count within the needle. He has no alternative other than unloading and reloading the needle within the operating room or X-raying the needle. Both methods are time consuming and therefore costly, especially since it requires hand loading of the radioactive seeds back into their cartridge. Nor is the handling of the seeds desirable.

One solution to the seed-counting problem is disclosed in a brachytherapy needle loading device called the "Express Loader" developed by Indigo Medical, Inc., of Cincinnati, Ohio, a Johnson & Johnson Company. That device provides a sliding radiation shield that enables magnified, see-through verification of the number of seeds to be loaded into the needle. More particularly, the seeds are housed in a plastic, transparent or at least translucent housing and that housing is covered by a cylindrical radiation shield. When the shield is telescopically retracted with respect to the housing, the number of seeds in the housing may be counted.

However, this express loader is expensive and only offered to certain physicians if they buy the seeds and loading service supplied by Johnson & Johnson.

What is needed, then, is a brachytherapy seed verification system that enables a physician to count the number of seeds and spacers within the pre-loaded needle to verify the correct number without requiring removal of the seeds and manually reloading the needle.

However, in view of the prior art taken as a whole at the time the present invention was made, it was not obvious to those of ordinary skill in this art how the needed device could be provided.

SUMMARY OF THE INVENTION

The long-standing but heretofore unfulfilled need for a brachytherapy verification device that enables the counting or visual verification of the seeds and spacers within a brachytherapy needle includes a needle having a sharp distal end and a lumen adapted to slidingly receive therein a plurality of said seeds and spacers. An adapter means such as a LUER LOK® adapter is secured to a proximal end of the needle. A clear plastic tube has a distal end received within a hollow interior of the adapter means and a hub aligns a lumen of the tube with the lumen of the needle. An elongate plunger rod is adapted to be slideably introduced into the lumen of the tube from a proximal end of the tube. The clear plastic tube has a lumen of substantially the same diameter as the lumen of the needle. When the assembly is positioned with the distal end of the needle pointing upwardly, and the plunger rod is retracted so that it does not occupy the lumen of the clear plastic tube, the seeds and spacers within the lumen of the needle slide under the influence of gravity into the lumen of the tube. The number of said seeds and spacers may then be visually ascertained by inspection of the contents of the clear plastic tube.

The hub is secured to a proximal end of the adapter means and serves to align the lumen of the clear plastic tube with the lumen of the needle.

The novel method for checking and verifying the number of seeds and spacers in a brachytherapy needle includes the steps of mounting an adapter means of hollow construction to a proximal end of an elongate needle. A distal end of a clear plastic tube is inserted into a proximal end of the adapter means. The lumen of the needle and the lumen of the clear plastic tube are dimensioned so that the lumens share a common diameter and abut each other. The lumen of the clear plastic tube is aligned with the lumen of the needle. A plunger rod is adapted to be slidingly introduced into a proximal end of the clear plastic tube, but it is substantially withdrawn from the clear plastic tube when the seeds and spacers are to be verified. The distal end of the needle is then pointed upwardly so that seeds and spacers in the lumen of the needle slide therefrom under the influence of gravity into the lumen of the clear plastic tube. The quantity of the seeds and spacers is then visually ascertainable.

A second embodiment includes an assembly that enables visual verification of bone wax, seeds, and spacers in a brachytherapy needle. It includes a needle having a sharp distal end and a lumen adapted to slidingly receive therein bone wax and a plurality of radioactive seeds and spacers. An adapter means of hollow construction is secured to a proximal end of the needle. A stylet adapted to be slidingly introduced into a proximal end of the adapter means and hence into a proximal end of the needle is provided. The assembly further includes a clear plastic tube having a lumen of sufficient diameter to slidingly receive therewithin the needle and an elongate plunger rod adapted to be slideably introduced into the lumen of the clear plastic tube from a proximal end thereof. The hub of the first embodiment is not present in the second embodiment.

The method of the second embodiment includes the steps of mounting an adapter means of hollow construction to a proximal end of an elongate needle. A clear plastic tube having a lumen of sufficient diameter is provided to slideably receive the elongate needle. A plunger rod having an external diameter less than the diameter of the lumen of the needle is provided and introduced through the lumen of the clear plastic tube and into the lumen of the needle. The plunger is substantially withdrawn from the lumen of the clear plastic tube when the seeds and spacers are to be verified. The distal end of the needle is pointed downwardly so that seeds and spacers in the lumen of the needle slide therefrom under the influence of gravity into the lumen of the clear plastic tube so that the quantity of said seeds and spacers is visually ascertainable.

A second method performed by the assembly of the second embodiment includes a method of checking and verifying the bone wax that seals the seeds and spacers in the needle during transportation as well as the number of seeds and spacers. This method includes the steps of mounting an adapter means of hollow construction to a proximal end of an elongate needle. A clear plastic tube having a lumen of sufficient diameter to slideably receive the elongate needle is provided. Also provided is a plunger rod having an external diameter less than the diameter of the lumen of the clear plastic tube. The plunger rod is adapted for sliding introduction into the lumen of the clear plastic tube. The plunger rod is substantially withdraw from the lumen of the clear plastic tube and a stylet is introduced into a proximal end of the elongate needle. The stylet pushes a string of bone wax, seeds and spacers out of the lumen of the elongate needle and into the lumen of the clear plastic tube so that the bone wax, seeds, and spacers may be visually verified. The string of bone wax, seeds and spacers is pushed out of the clear plastic tube and into the lumen of the elongate needle by introducing the plunger rod into a proximal end of the clear plastic tube. The clear plastic tube and the plunger rod are then removed so that the elongate needle is usable in a brachytherapy procedure.

An important object of this invention is to significantly advance the art of brachytherapy needles by providing a brachytherapy needle construction that enables a physician to quickly and accurately ascertain the number of unimplanted radioactive seeds without removing the seeds from the needle.

Another object is to provide an easy method for visually ascertaining a string of bone wax, seeds, and spacers in a brachytherapy needle.

The invention accordingly comprises the features of construction, combination of elements, and arrangement of parts that will be exemplified in the description set forth hereinafter, and the scope of the invention will be set forth in the claims.

BRIEF DESCRIPTION OF THE DRAWINGS

For a fuller understanding of the nature and objects of the invention, reference is made to the following detailed description, taken in connection with the accompanying drawings, in which:

FIG. 1 is an exploded side elevational view of a plurality of seeds and spacers disposed in axial alignment with one another and in axial alignment with a lumen of a brachytherapy needle;

FIG. 2 is a longitudinal sectional view of the brachytherapy needle of FIG. 1 when a plurality of seeds and spacers are disposed within the lumen of said needle;

FIG. 3 is an exploded side elevational view of the needle of FIGS. 1 and 2, together with the novel hub, clear plastic tube, and a plunger rod;

FIG. 4 is a longitudinal sectional view depicting the parts of FIG. 3 when the needle has been inverted and the seeds and spacers have slid into the clear plastic tubing so that they can be counted;

FIG. 5 is a longitudinal sectional view of a second embodiment having some of the same parts as the first embodiment but arranged in a different configuration;

FIG. 6 is a side elevational view of the parts depicted in FIG. 5 but with the plunger rod retracted; and FIG. 7 is a longitudinal sectional view of the parts depicted in FIG. 6.

DETAILED DESCRIPTION OF THE PREFERRED EMBODIMENT

Referring now to FIG. 1, it will there be seen that needle 10 has a sharp distal end 12 and an adapter means 14 fixedly secured to its proximal end. In a preferred embodiment, the adapter means is a LUER LOK® adapter because such adapter is in widespread use and is therefore familiar to physicians.

A plurality of seeds and spacers, collectively denoted 16, are depicted in axial alignment with one another and with lumen 11 of needle 10. As indicated by directional arrow 18, seeds and spacers 16 are positioned within said lumen when a brachytherapy procedure begins.

FIG. 2 depicts seeds and spacers 16 when fully loaded into lumen 11.

FIGS. 3 and 4 depict a novel hub 20 that engages a trailing or proximal end of adapter 14. Hub 20 has a tube-in-tube construction, as best understood in connection with FIG. 3. Outer tube 22 engages an exterior surface of adapter 14 at its trailing end and inner tube 24 is slideably received within interior chamber 26 of the adapter.

As indicated by directional arrow 27 in FIG. 3, clear plastic tube 28 is slidingly introduced into the proximal end of hub 20 when the parts of this first embodiment are assembled together. More particularly, the distal end of clear plastic tube 28 is slideably received within inner tube 24 as depicted in FIG. 4 and abuts the distal end of interior chamber 26. A suitable adhesive is used to maintain the distal end of clear plastic tube 28 in this position. The distal end 30 of clear plastic tube 28 is in closely spaced, axial alignment with the proximal end of needle 10. A careful inspection of FIG. 4 reveals that lumen 11 of needle 10 and lumen 29 of clear plastic tube 28 share a relatively common diameter and are in axial alignment with one another. Accordingly, as depicted in FIG. 4, when needle 10 is inverted, i.e., when distal end 12 thereof is pointed straight up, seeds and spacers 16 within lumen 11 of needle 10 slide into lumen 29 of clear plastic tube 28 under the influence of gravity.

As is also clear from FIG. 4, seeds and spacers 16 cannot slide from lumen 11 of needle 10 unless plunger rod 32 is withdrawn from lumen 29 of clear plastic tube 28. Plunger rod 32, having handle 34 at its proximal end, is slidingly received within lumen 29 of clear plastic tube 28, as depicted in FIG. 3, when the seeds and spacers are fully loaded into lumen 11 of needle 10. This prevents movement of the seeds and spacers during shipment of the novel apparatus.

Handle 36 at the proximal end of clear plastic tube 28 has a first axial bore 38 formed therein that slideably receives plunger rod 32. Boss 40 is formed integrally with handle 36 and stabilizes the proximal end of clear plastic tube 28. The proximal end of clear plastic tube is slideably received within an unnumbered second axial bore having a diameter slightly greater than that of first axial bore 38 to accommodate clear plastic tube 28. An enlargement, not depicted, is formed on the distal end of plunger rod 32 so that said plunger rod cannot be fully retracted from first axial bore 38. Any other suitable mechanical means for preventing full retraction of the distal end of plunger rod 32 from handle 36 is within the scope of this invention.

Essentially the same parts are arranged differently with respect to one another in the second embodiment of FIGS. 5–7. Accordingly, the same reference numerals are used to indicate the same parts so that said parts need not be described a second time. However, lumen 29 of clear plastic tube 28 is denoted 29a in this embodiment and clear plastic tube 28 is denoted 28a because said lumen 29a is larger in this embodiment than in the first embodiment. Specifically, as indicated in FIGS. 5–7, lumen 29a is sufficiently large to slideably receive therewithin needle 10. Instead of the distal end 30 of clear plastic tube 28 being received within the proximal end of adapter 14, the lumen 29a of clear plastic tube 28a slideably receives therein needle 10. In other words, as indicated in FIGS. 5–7, handle 36 of clear plastic tube 28a is disposed in confronting relation to adapter means 14 of needle 10.

To use the second embodiment, plunger 32 is fully retracted as depicted in FIGS. 6 and 7 and the sharp point 12 of needle 10 is positioned downwardly so that the seeds and spacers in said needle 10 slide into clear plastic tube 28a under the influence of gravity If bone wax is used to seal the end of needle 10, said bone wax is pushed, together with the seeds and spacers, into clear plastic tube 28a with a stylet, not shown, that is introduced into the proximal end of adapter 14. When a stylet is used, there is no need to orient the needle so that its point is pointing downwardly. When the entire string of bone wax, seeds, and spacers has been verified visually, plunger rod 32 is pushed into lumen 29a of clear plastic tube 28a and said bone wax, seeds, and spacers are returned to lumen 11 of needle 10. Clear plastic tube 28 and plunger rod 32 are then removed and needle 10 is used in a conventional manner.

It will thus be seen that the objects set forth above, and those made apparent from the preceding description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. An assembly that enables the counting of the seeds and spacers in a brachytherapy needle, comprising:
   a needle having a sharp distal end and a lumen adapted to slidingly receive therein a plurality of radioactive seeds and spacers;
   an adapter means of hollow construction secured to a proximal end of said needle;
   a tube having a distal end received within a hollow interior of said adapter;
   a hub means for aligning a lumen of said tube with the lumen of said needle;
   a plunger rod adapted to be slideably received within said tube;
   said tube formed of a material that is sufficiently translucent to enable visual inspection of said lumen of said tube;
   said lumen of said tube having substantially the same diameter as the lumen of said needle so that when said assembly is positioned with the distal end of said needle pointing upwardly, the seeds and spacers within said lumen of said needle slide under the influence of gravity into the lumen of said tube so that the number of said seeds and spacers may be visually ascertained.

2. The assembly of claim 1, further comprising:
   said hub means secured to a proximal end of said adapter;
   an outer pan of said hub means engaging an exterior surface of said adapter;
   an inner part of said hub means received within a hollow interior of said adapter;
   said inner part of said hub means adapted to slidingly receive said tube so that a distal end of said tube abuts said hollow interior of said adapter;
   whereby said hub means aligns said lumen of said tube with the lumen of said needle.

3. The assembly of claim 2, further comprising an adhesive means for securing a distal end of said tube to said hollow interior of said adapter.

4. The assembly of claim 1, further comprising:
   a handle mounted to a proximal end of said tube;
   said handle having a boss integrally fanned therein;
   a first axial bore formed in said handle;
   a second axial bore formed in said boss, said second axial bore having a larger diameter than said first axial bore and said second axial bore adapted to receive the proximal end of said tube.

5. The assembly of claim 4, further comprising:
   said first axial bore adapted to slideably receive said plunger rod;
   said plunger rod having an outer diameter slightly less than a diameter of said lumen of said tube;
   a handle formed at a proximal end of said plunger rod;
   whereby manipulation of said plunger rod handle enables insertion and retraction of said plunger rod into and out of the lumen of said tube, respectively.

6. The assembly of claim 5, wherein a distal end of said plunger rod is adapted so that said distal end of said plunger rod is not fully retractable from said tube.

7. The assembly of claim 1, wherein said tube is formed of a clear plastic.

8. The assembly of claim 1, wherein said tube is formed of a clear plastic.

9. A method of checking and verifying the number of seeds and spacers in a brachytherapy needle, comprising the steps of:
   mounting an adapter of hollow construction to a proximal end of a needle;
   inserting a distal end of a clear tube into a proximal end of said adapter;
   dimensioning the lumen of the needle and the lumen of the clear tube so that said lumens share a common diameter;
   aligning the lumen of the clear tube with the lumen of the needle;
   inserting a plunger rod into a proximal end of said clear tube;
   dimensioning said plunger rod so that no seeds and spacers can enter into the lumen of said clear tube from the lumen of said needle when said plunger rod is filly received within the lumen of said clear tube;
   substantially withdrawing the plunger from the clear tube and pointing the distal end of the needle upwardly so that seeds and spacers in the lumen of said needle slide therefrom under the influence of gravity into the lumen of said clear tube so that the quantity of said seeds and spacers is visually ascertainable.

10. The assembly of claim 8, further comprising:
    a handle mounted to a proximal end of said tube;
    said handle having a boss integrally formed therein;
    a first axial bore formed in said handle;
    a second axial bore formed in said boss, said second axial bore having a larger diameter than said first axial bore and said second axial bore adapted to receive the proximal end of said tube.

11. The assembly of claim 10, further comprising:
    said first axial bore adapted to slideably receive said plunger rod;

said plunger rod having an outer diameter slightly less than a diameter of said lumen of said tube;

whereby manipulation of said plunger rod enables insertion and retraction of said plunger rod into and out of the lumen of said tube, respectively.

12. The assembly of claim 11, wherein a distal end of said plunger rod is adapted so that said distal end of said plunger rod is not fully retractable from said tube.

13. The assembly of claim 12, further comprising:

a plunger rod handle means secured to a proximal end of said plunger rod to facilitate said insertion and retraction of said plunger rod.

14. An assembly that enables visual verification of bone wax, seeds, and spacers in a brachytherapy needle, comprising:

a needle having a sharp distal end and a lumen adapted to slidingly receive therein bone wax and a plurality of radioactive seeds and spacers;

an adapter of hollow construction secured to a proximal end of said needle;

a stylet adapted to be slidingly introduced into a proximal end of said adapter and hence into a proximal end of said needle;

a tube having a lumen of sufficient diameter to slidingly receive therewithin said needle;

an elongate plunger rod adapted to be slideably introduced into said lumen of said tube from a proximal end thereof; and said tube formed of a material that is sufficiently translucent to enable visual inspection of items positioned with said lumen of said tube.

15. A method of checking and verifying the number of seeds and spacers in a brachytherapy needle, comprising the steps of:

mounting an adapter of hollow construction to a proximal end of a needle;

providing a clear tube having a lumen of sufficient diameter to slideably receive said needle;

providing a plunger rod having an external diameter less than the diameter of said lumen of said clear tube and introducing said plunger rod into said lumen of said clear tube;

dimensioning said plunger rod so that no seeds and spacers can enter into the lumen of said clear tube from the lumen of said needle when said plunger rod is fully received within the lumen of said clear tube;

substantially withdrawing the plunger from the clear tube and pointing the distal end of the needle downwardly so that seeds and spacers in the lumen of said needle slide therefrom tinder the influence of gravity into the lumen of said clear tube so that the quantity of said seeds and spacers is visually ascertainable.

16. A method of checking and verifying the number of seeds and spacers in a brachytherapy needle, comprising the steps of:

mounting an adapter of hollow construction to a proximal end of a needle;

providing a clear tube having a lumen of sufficient diameter to slideably receive said needle;

providing a plunger rod having an external diameter less than the diameter of said lumen of said clear tube, said plunger rod being adapted for sliding introduction into said lumen of said clear tube;

dimensioning said plunger rod so that no seeds and spacers can enter into the lumen of said clear tube from the lumen of said needle when said plunger rod is fully received within the lumen of said clear tube;

substantially withdrawing the plunger rod from the clear tube;

introducing a stylet into a proximal end of said needle and pushing a string of bone wax, seeds and spacers out of the lumen of said needle and into the lumen of said clear tube so that said bone wax, seeds, and spacers may be visually verified;

pushing said string of bone wax, seeds and spacers out of said clear tube and into said lumen of said elongate needle by introducing said plunger rod into a proximal end of said clear tube; and removing said clear tube and plunger rod so that said needle is usable in a brachytherapy procedure.

* * * * *